(12) United States Patent
Smith et al.

(10) Patent No.: US 9,068,163 B2
(45) Date of Patent: *Jun. 30, 2015

(54) METHODS AND COMPOSITIONS FOR GROWTH OF EMBRYONIC STEM CELLS

(75) Inventors: Gary D. Smith, Ann Arbor, MI (US); Joerg Lahann, Ann Arbor, MI (US); Jun Ding, Ann Arbor, MI (US); Himabindu Nandivada, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 740 days.

This patent is subject to a terminal disclaimer.

(21) Appl. No.: 12/530,126

(22) PCT Filed: Mar. 7, 2008

(86) PCT No.: PCT/US2008/056252
§ 371 (c)(1),
(2), (4) Date: Nov. 30, 2009

(87) PCT Pub. No.: WO2008/112560
PCT Pub. Date: Sep. 18, 2008

(65) Prior Publication Data
US 2010/0068810 A1      Mar. 18, 2010

Related U.S. Application Data

(60) Provisional application No. 60/906,012, filed on Mar. 9, 2007.

(51) Int. Cl.
*C12N 5/02* (2006.01)
*C12N 5/0735* (2010.01)
*C12N 5/00* (2006.01)

(52) U.S. Cl.
CPC ................ *C12N 5/0606* (2013.01); *C12N 5/00* (2013.01); *C12N 2533/30* (2013.01)

(58) Field of Classification Search
CPC ........ C12N 5/06; C12N 5/00; C12N 2533/30; C12N 2533/00
USPC .......................................... 435/377, 395, 404
See application file for complete search history.

(56) References Cited

U.S. PATENT DOCUMENTS 5,906,934 A      5/1999 Grande et al.

OTHER PUBLICATIONS

Konno et al. J. of Bioscience & Engineering, 102(4): 304-310, 2006.*
Lim et al. Proteomics, 2:1187-1203, 2002.*
Prowse et al. Proteomics, 5:978-989, 2005.*
Thomson et al. PNAS, 92:7844-7848, Aug. 1995.*
NIH. Stem Cells: Scientific Progress and Future Research Directions, Department of Health and Human Services, Chapter 1, pp. 1-4, Jun. 2001.*
Cao et al. J. of Exp. Zoo., 311A: 368-376, 2009.*
Brevini et al. Theriogenology, 74: 544-550, 2010.*
Paris et al. Theriogenology, 74: 516-524, 2010.*
Takahashi et al., Cell, 131: 12-12, Nov. 30, 2007.*
Amit et al., "Human feeder layers for human embryonic stem cells" 2003 Biol. Repro. 68:2150-2156.
Amit et al., "Feeder layer- and serum-free culture of human embryonic stem cells" 2004 Biol. Repro. 70:837-845.
Arasawa et al., "Grafting of zwitterion-type polymers onto silica gel surface and their properties" 2004 Reactive and Function Polymers 61: 153.
Azzaroni et al., "USCT wetting transitions of polyzwitterionic brushes driven by self-association" 2006 Angewandte Chemie, International Edition 45, 1770-1774.
Beattie et al., "Activin A maintains pluripotency of human embryonic stem cells in the absence of feeder layers" 2005 Stem Cells 23:489-495.
Brimble et al., "Karyotypic stability, genotyping, differentiation, feeder-free maintenance, and gene expression sampling in three human embryonic stem cell lines derived prior to Aug. 9, 2001" 2004 Stem Cells 13:585-597.
Cho et al., "Highly efficient non-biofouling coating of zwitterionic polymers: poly((3-(methacryloylamino)propyl)-dimethyl(3-sulfopropyl)ammonium hydroxide)" 2007 Langmuir 23, 5678-5682.
Draper et al., "Recurrent gain of chromosomes 17q and 12 in cultured human embryonic stem cells" 2004 Nat. Biotech. 22:53-54.
Ellerstrom et al., "Derivation of a xeno-free human embryonic stem cell line" 2006 Stem Cells 24:2170-2176.
Harris et al., "Zwitterions: Proof of the zwitterion constitution of the amino-acid molecule. II. Amino-acids, polypeptides, etc., and proteins as zwitterions, with instances of non-zwitterion ampholytes" 1930 Biochemical J. 24:1080.
Imreh et al., "In vitro culture conditions favoring selection of chromosomal abnormalities in human ES cells" 2006 J. Cell Biochem. 99:508-516.
Jiang et al., "Platelet adhesive resistance of polyurethane surface grafted with zwitterions of sulfobetaine" 2004 Colloids Surf B Biointerfaces 36, 19-26.
Klimanskaya et al., "Human embryonic stem cells derived without feeder cells" 2005 Lancet 365:1636-1641.
Li et al., "Hydrogels as Artificial Matrices for Human Embryonic Stem Cell Self-Renewal" 2006 J. Biomed. Mater. Res. vol. 79A pp. 1-5.
Longo et al., "The chromosome make-up of mouse embryonic stem cells is predictive of somatic and germ cell chimaerism" 1997 Transgenic Res. 6:321-328.
Maitra et al., "Genomic alterations in cultured human embryonic stem cells" 2005 Nat. Genet. 37:1099-1103.
Mallon et al., "Toward xeno-free culture of human embryonic stem cells" 2006 Int. J. Biochem. Cell Biol. 38:1063-1075.
Matsubara et al., "A New Technique to Expand Human Mesenchymal Stem Cells Using Basement Membrane Extracellular Matrix." 2004 Biochem. Biophys. Res. Comm. vol. 313 pp. 503-508.

(Continued)

*Primary Examiner* — Thaian N Ton
(74) *Attorney, Agent, or Firm* — Casimir Jones, S.C.

(57) ABSTRACT

The present invention provides methods and compositions for establishing and maintaining growth of undifferentiated stem cells. In particular, the present invention provides synthetic growth matrices for stem cells, wherein said cells are capable of going through multiple passages while remaining in an undifferentiated state.

3 Claims, 6 Drawing Sheets

(56) References Cited

OTHER PUBLICATIONS

Mwale et al., "Suppression of Genes Related to Hypertrophy and Osteogenesis in Committed Human Mesenchymal Stem Cells Cultures on Novel Nitrogen-Rich Plasma Polymer Coatings." 2006 Tissue Engineering vol. 12 No. 9 pp. 2639-2647.
Skottman et al., "Culture conditions for human embryonic stem cells" 2006 Reproduction 132:691-698.
Stojkovic et al., "An autogeneic feeder cell system that efficiently supports growth of undifferentiated human embryonic stem cells" 2005 Stem Cells 23:306-314.
Thomson et al., "Embryonic stem cell lines derived from human blastocysts" 1998 Science 282:1145-1147.
Ullmann et al., "Epithelial-mesenchymal transition process in human embryonic stem cells cultured in feeder-free conditions" 2007 Mol. Human. Repro. 13:21-32.
Ware et al., "Controlled-rate freezing of human ES cells" 2005 Biotechniques 38:879-884.
Xu et al., "Feeder-free growth of undifferentiated human embryonic stem cells" 2001 Nat. Biotechnol 19:971-974.
Yuan et al., "Polyurethane vascular catheter surface grafted with zwitterionic sulfobetaine monomer activated by ozone" 2004 Colloids Surf B Biointerfaces 35, 1-5.
Zhao et al. 2000 Progress in Polymer Sci 25:677.
Jing et al., "Hematopoietic stem cells in co-culture with mesenchymal stromal cells—modeling the niche compartments in vitro," Haemalogica, 2010, 95:542-550.
Ludwig et al., "Derivation of human embryonic stem cells in defined conditions," Nature Biotechnology, 2005, 24 (2):185-187.
The Sigma-Aldrich catalog, http://sigmaaldrich.com/catalog/, accessed online on Jun. 4, 2010, "neural stem cells" and "Stemline Neural Stem Cell Expression Medium."

* cited by examiner

A

B

METHODS AND COMPOSITIONS FOR GROWTH OF EMBRYONIC STEM CELLS

CROSS-REFERENCE TO RELATED APPLICATIONS

The present application is a U.S. 371 national stage entry of pending International Patent Application No. PCT/US2008/056252, filed Mar. 7, 2008, which claims priority to U.S. Provisional Application 60/906,012, filed Mar. 9, 2007, all of which are herein incorporated by reference in their entireties.

STATEMENT REGARDING FEDERALLY SPONSORED RESEARCH OR DEVELOPMENT

This invention was made with government support under grant no. 1P20GM069985-01 awarded by the National Institute of General Medical Sciences. The government has certain rights in the invention.

FIELD OF THE INVENTION

The present invention provides methods and compositions for establishing and maintaining growth of undifferentiated stem cells, such as embryonic stem cells. In particular, the present invention provides synthetic growth matrices for stem cells, wherein said cells are capable of going through multiple passages while remaining in an undifferentiated state.

BACKGROUND OF THE INVENTION

Human and other mammalian stem cells including embryonic stem cells (hESCs and ESCs), which are pluripotent cells derived from pre-implantation embryos, have enormous potential as predicative models of early development or for cell replacement therapies (Draper et al., 2004, Stem Cells & Devel. 13:325-336). Because hESCs show remarkable sensitivity towards environmental influences, their continuous undifferentiated growth has been a major challenge undermining widespread use of hESCs in many applications. Currently, sustained hESC cultures still require naturally-derived cell substrates, such as mouse or human embryonic fibroblast cells, MATRIGEL, laminin, or fibronectin (Draper et al. 2004; Stojkovic et al., 2005, Stem Cells 23:306-314; Xu et al., 2001, Nat. Biotech. 19:971-974; Mallon et al., 2006, Int. J. Biochem. Cell Biol. 38:1063-1075; Amit et al., 2004, Biol. Repro. 70:837-845; Amit et al., 2003, Biol. Repro. 68:2150-2156; Skottman et al., 2006, Reproduction 132:691-698; Thomson et al., Science 282:1145-1147; Ellerstrom et al., 2006, Stem Cells 24:2170-2176; Xu et al., 2001, Nat. Biotechnol 19:971-974; Cheon et al., 2006, Biol. Reprod. 74:611; Beattie et al., 2005, Stem Cells 23:489-495).

However, xenogenic culture matrices are associated with several shortcomings. While co-culture systems with fibroblasts complicate direct studies of self-renewal and/or differentiation mechanisms of hESCs, cell substrates based on MATRIGEL and other naturally derived matrices show batch-to-batch inconstancies and may be prone to contaminations. To address these challenges, synthetic polymers have been proposed as cell culture substrates of hESC, because of their well-defined and reproducible fabrication, but have not yet been established for long-term hESC cultures.

As such, what are needed are compositions and methods that provide an environment for growth and maintenance of embryonic stem cells. The establishment of defined microenvironments for stem cell culture addresses a major issue of human embryonic stem cell research, and will provide embryonic stem cells useful in, for example, research purposes and potential clinical treatments of diseases.

SUMMARY OF THE INVENTION

The present invention provides methods and compositions for establishing and maintaining growth of undifferentiated stem cells. In particular, the present invention provides synthetic growth matrices for stem cells, wherein said cells are capable of going through multiple passages while remaining in an undifferentiated state.

Certain illustrative embodiments of the invention are described below. The present invention is not limited to these embodiments.

In one embodiment, the present invention provides artificial polymer matrices for use in cultures stem cells (e.g., embryonic stem cells (ESCs) or adult stem cells). In some embodiments, such matrices support ESC colony formation, proliferation and maintenance of a pluripotent state. In one embodiment, the artificial polymer matrices are comprised of synthetic hydrogels. In some embodiments, the present invention provides artificial polymer matrices fabricated without the addition of naturally derived biomolecules, such as extracellular matrix components, growth factors, laminin, matrigel, fibronection, vitronectin, collagen, gelatin, and so on. In some embodiments, the artificial polymer matrix comprises negatively charged groups, such as phosphate groups, sulfate groups, carboxyl groups, sulfonate groups, phosphonate groups, and the like. In some embodiments, the artificial polymer matrices may further comprise positively charged groups, such as ammonium groups, and the like. In some embodiments, the artificial polymer matrices comprise simultaneously positively and negatively charged groups. In some embodiments, the artificial polymer matrices comprise, at least in part, zwitterionic groups (e.g., sulfobetaine). For example, zwitterionic groups are combined with other charged groups, such as positively and/or negatively charged groups. The matrix may comprise one or more types of zwitterionic groups. The incorporation of zwitterionic groups into the artificial polymer matrices allows the materials to engage in strong inter- and intramolecular deipolar interactions which span from a non-associated to a fully associated regime, behavioral characteristic for zwitterionic molecules. In one embodiment of the present invention the artificial polymer matrices comprise one, or more than one, type of zwitterionic group. In some embodiments, the zwitterionic group is

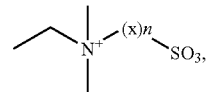

where x is any aliphatic or substituted aliphatic chain, aryl or substituted aryl chain, or hydrogen; and n is an integer of 1 or greater. In other embodiments the artificial polymer matrix comprises sulfobetaine groups. In some embodiments, the present invention provides a synthetic cell matrix system comprising, for example, poly[2-(methacryloyloxy)ethyl dimethyl(3-sulfopropyl)ammonium] (PMEDSAH) hydrogels or copolymers or blends thereof, or functional equivalents thereof, that supports long-term proliferation and passaging of hESCs. For example, during development of embodiments of the present invention, hESCs were subjected to at least eighteen continuous passages over a period of approximately seven months without undergoing unregulated differentiation. For example, hESCs cultured on PMEDSAH hydrogels retained normal karyotypes and continuously and consistently displayed the markers of undifferentiated hESCs. This is the first time that hESCs exhibited undifferentiated growth and passaging for extended times on fully synthetic cell matrices void of any xenogenic or previously used components.

In one embodiment, the artificial polymers form, for example, a three-dimensional polymer matrix structure. In yet another embodiment, biomolecules are further immobilized into the artificial polymer matrix. In some embodiments, biomolecules include, but are not limited to, small molecules for cell based therapies and treatments, drug delivery, and the like. In some embodiments, such polymer matrix structures provide, for example, scaffolds for cell growth for tissue regeneration.

In one embodiment, the present invention provides for the use of a synthetic hydrogel matrix comprising glycoproteins in growing and maintaining stem cells (e.g., embryonic stem cells or adult stem cells) in a pluripotent state, with native karyotype, for multiple passages. In some embodiments, the present invention provides for methods of culturing stem cells comprising providing stem cells, applying the stem cells to a substrate that has been treated with a synthetic hydrogel as previously described, and growing the stem cells on the substrate such that their pluripotency and native karyotype is maintained. In some embodiments, culture methods further comprise the use of a fully defined media.

In some embodiments, the present invention provides for compositions and methods of culturing stem cells for use in drug screening. In some embodiments, the present invention provides compositions and methods for culturing stem cells for use in screening for modulators of stem cell differentiation. In some embodiments, the present invention provides compositions and methods for culturing stem cells for use in research applications. In some embodiments, the present invention provides compositions and methods for culturing stem cells for use in clinical applications, such as determining compositions, drugs, small molecules, useful for, for example modulating stem cells for subsequent use in transplantation or treatment of diseases (e.g., leukemia, liver disease, brain diseases, proliferative diseases, etc).

In some embodiments, the present invention provides for compositions and methods for culturing embryos using the substrates described herein and optionally culture media suitable for culture of embryos.

DEFINITIONS

Figure 1:
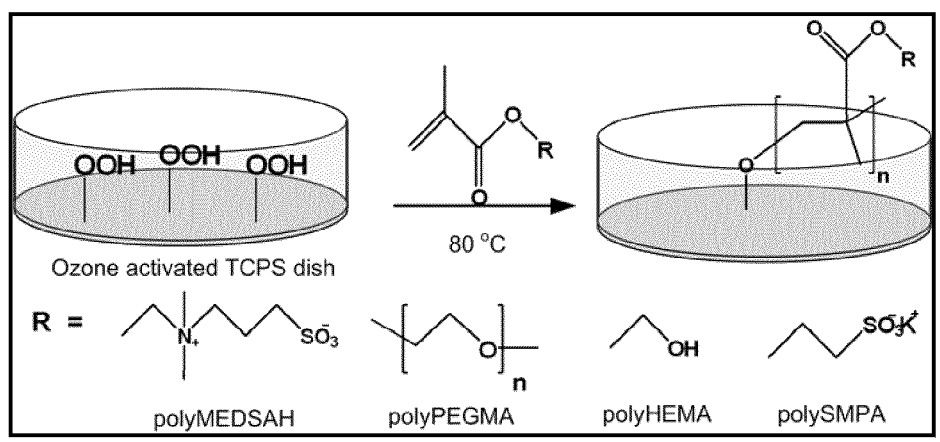
FIG. 1 shows exemplary compositions attached TCPS dishes, thereby creating substrates that are coated with different synthetic polymer matrices.

As used herein, the term "multiple passages", "multiple passaging", and/or "multiple mechanical passages or passaging", refers to the number of times a cell is grown in vitro on a tissue culture substrate, released from that substrate, and reapplied to another substrate. For example, the present invention described embodiments where human embryonic stem cells were passaged numerous, thereby demonstrating that cells can be applied to a substrate, released from a substrate, and reapplied to another substrate while still allowing for growth and maintenance of the cell culture.

As used herein, the term "substrate" refers to a surface for cell culture. A substrate can be, for example, a glass slide, a culture dish, culture plates, glass or composite beads, chip microchannels, and the like. The present invention is not limited by the type of substrate used.

The term "chemical moiety" refers to any chemical compound containing at least one carbon atom. Examples of chemical moieties include, but are not limited to, aromatic chemical moieties, chemical moieties comprising Sulfur, chemical moieties comprising Nitrogen, hydrophilic chemical moieties, and hydrophobic chemical moieties.

As used herein, the term "aliphatic" represents the groups including, but not limited to, alkyl, alkenyl, alkynyl, alicyclic.

As used herein, the term "aryl" represents a single aromatic ring such as a phenyl ring, or two or more aromatic rings (e.g., bisphenyl, naphthalene, anthracene), or an aromatic ring and one or more non-aromatic rings. The aryl group can be optionally substituted with a lower aliphatic group (e.g., alkyl, alkenyl, alkynyl, or alicyclic). Additionally, the aliphatic and aryl groups can be further substituted by one or more functional groups including, but not limited to, —NH$_2$, —NHCOCH$_3$, —OH, lower alkoxy (C$_1$-C$_4$), halo (—F, —Cl, —Br, or —I).

As used herein, the term "substituted aliphatic," refers to an alkane, alkene, alkyne, or alicyclic moiety where at least one of the aliphatic hydrogen atoms has been replaced by, for example, a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such include, but are not limited to, 1-chloroethyl and the like.

As used herein, the term "linker" refers to a chain containing up to and including eight contiguous atoms connecting two different structural moieties where such atoms are, for example, carbon, nitrogen, oxygen, or sulfur.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

The term "sample" as used herein is used in its broadest sense. A sample suspected of indicating a condition characterized by the dysregulation of apoptotic function may comprise a cell, tissue, or fluids, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the terms "purified" or "to purify" refer to the removal of undesired components from a sample. As used herein, the term "substantially purified" refers to molecules that are at least 60% free, preferably 75% free, and most preferably 90%, or more, free from other components with which they usually associated.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., the level of dysregulation of apoptosis in a cell or tissue). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In some embodiments, "test compounds" are agents that modulate apoptosis in cells.

DETAILED DESCRIPTION OF THE INVENTION

Certain illustrative embodiments of the invention are described below. The present invention is not limited to these embodiments.

The chemistry and morphology of the microenvironment surrounding a human embryonic stem cell plays an important role in the cellular behavior, controlling the orchestration of various developmental events, such as cell proliferation, differentiation, migration, and apoptosis. Given the importance of the chemical signature of the microenvironment, the development of fully-defined synthetic matrices is an important step towards fully synthetic cell culture systems, but will largely depend on materials selection for the cell substrate. Several synthetic polymers, such as PLGA, PLA, and PNIPAM-based polymers, as well as polymers obtained using combinatorial methods, have been previously evaluated. While these studies contributed to a fundamental appreciation of the importance of the chemical identity of the microenvironment, they fall short in reporting long-term undifferentiated growth and passaging of hESCs.

In developing embodiments of the present invention, functionally diverse groups of synthetic hydrogels and their use in hESCs adhesion studies were identified, and their subtle interrelationships between synthetic polymer matrices and hESCs, for example, were examined. Four hydrogels comprising identical methacrylate backbone structures, but different side chain chemistries, were deposited onto the surface of tissue culture styrene (TCPS) dishes via surface-initiated graft-polymerization. The resulting synthetic polymers were hydrogels with high to moderate hydrophilicity. On the basis of their side chain chemistries, these materials are classified as hydrogen-bond acceptors (PHEMA), hydrogen-bond donors (PPEGMA), charge-donors (PSMPA), or polyzwitterions (e.g., PMEDSAH) (FIG. 1).

Artificial polymer matrices can be deposited onto the surface of a substrate, for example, using standard methods known to one skilled in the art. These methods may include surface physisorption or chemisorption. Physisorption includes, for example, the static and dynamic coating with polymers and/or oligomers. Chemisorption includes methods such as surface-initiated polymerization, grafting including grafting-from and grafting-to techniques, covalent tethering to the surface, crosslinking using exposure of the substrate to a solution of a polymer and/or oligomers followed by treatment with an energy source, such as plasma, UV, gamma radiation, ion beam, and the like.

Undifferentiated hESCs from cell lines H9 and BG01 growing on MEF as previously described (Thomson et al, 1998), were mechanically harvested and seeded onto the different hydrogel-coated plates. The surfaces were compared to solvent-casted poly(α-hydroxy esters), PLA, PLGA, and MATRIGEL coated substrates. Cell culture experiments were conducted in MEF-conditioned medium (MEF-CM) (Amit et al., 2003). Following initial hESC seeding, no cell attachment was observed on PLA, PLGA, the negatively charged PSPMA substrate, or PHEMA (Table 1).

TABLE 1

| Polymer | Contact angle | Attachment | Long term |
|---|---|---|---|
| polyMEDSA | 45 | + | + |
| polyHEMA | 55 | − | − |
| polyPEGMA | 60 | + | − |
| polySPMA | 80 | − | − |

TABLE 1-continued

| Polymer | Contact angle | Attachment | Long term |
|---------|--------------|------------|-----------|
| PLA | 9/33 | – | – |
| PLGA | | – | – |

In contrast, hESC attachment was observed on poly (ethylene glycol) methyl ether methacrylate (PEGMA), and unmodified TCPS plates; however colonies did not grow with time and/or hESCs spontaneously differentiated during the first or second passage. These data are consistent with the recently reported short-term self-renewal of hESCs on polymer matrices (Li et al., 2006, J. Biomad. Mater. Res. A 79:1-5). None of the hydrogels showed consistent long-term growth, consecutive passaging, and maintenance of long-term pluripotency. MATRIGEL-coated dishes and PMEDSAH hydrogel coatings supported initial cell adhesion and proliferation.

The physical and chemical properties of PMEDSAH coatings were characterized using a combination of surface analytical tools including X-ray photoelectron microscopy (XPS), Fourier transform infrared spectroscopy (FT-IR), imaging ellipsometry, and scanning probe microscopy (SPM). PMEDSAH films used had an average surface root mean square roughness of 0.91 nm as determined by SPM. Imaging ellipsometry showed PMEDSAH film thicknesses between 10 and 2000 nm. The polymer films were stable when stored for extended times in aqueous solutions. As such, it was concluded that the PMEDSAH coatings were characterized by ultra-thin, smooth polymer films chemically tethered to the TCPS substrate. FT-IR spectra showed distinct bands at 1724 $cm^{-1}$ indicating the presence of carbonyl groups characteristic of PMEDSAH. To further confirm initial evidence from the FT-IR studies that indicated the presence of twitterionic groups on the surface, the elemental surface composition of PMEDSAH coatings was quantified by X-ray photoelectron spectroscopy (XPS). The presence of characteristic peaks associated with nitrogen, sulfur, and oxygen, and the relative composition of these elements correlated well with the expected chemical composition of PMEDSAH. In addition, the high resolution $C_{1s}$ spectrum of PEDMSAH revealed characteristic signals associated with hydrocarbon ($\underline{C}$—H/C) peak at 285.0 eV, ammonium-bond carbon (—$\underline{C}$—$N^+(\underline{C}H_3)_2$—) at 286.4 eV, and ester carbon (—$\underline{C}OO$—) peak at 288.9 eV. Taken together, FTIR and XPS analysis confirms the overall chemical composition of PMEDSAH coating, and demonstrates the presence of twitterionic groups at the surface of the coating. Moreover, contact angle measurements revealed an advancing contact angle of above 45 degrees of the PMEDSAH coating, which is in accordance with a self-associated super-coiled regime. It was determined, therefore, that the PMEDSAH coatings used in developing embodiments of the present invention, have, for example, properties that distinguish them from the other hydrogel coatings.

Initial experiments revealed, for example, a positive influence of PMEDSAH hydrogels on human embryonic cell culture adhesion and proliferation when compared to other synthetic polymers. In additional experimentation, growth and passaging of hESC on PMEDSAH and MATRIGEL dishes over a period of 6 months was performed. Human ESCs were passaged multiple times (e.g., for example, up to 18 passages; i.e., greater than 2, 5, 10, 15 passages) and cell fate of hESCs was continuously monitored by immunostaining. It was observed that PMEDSAH hydrogels supported cell attachment, colony growth, and hESC proliferation for more than eight months (e.g., more than 1, 2, 4, 6, months) over multiple passages. Human ESCs were characterized at regular intervals throughout the course of experimentation. After 7 months (roughly 18 passages), hESCs cultured on PMEDSAH expressed pluripotency markers, such as OCT3/4, SOX-2, SSEA-4, TRA-1-60 and TRA-1-81 (FIG. 2A), and retained normal karyotypes. The latter is an important aspect, for example, because the long-term culture of mouse (Longo et al., 1997, Transgenic Res. 6:321-328) and human (Draper et al., 2004, Nat. Biotech. 22:53-54; Maitra et al., 2005, Nat. Genet. 37:1099-1103) ESCs can lead to distinct chromosomal abnormalities and hESC feeder-free culture may bias for occurrence in aneuploidy (Matira et al., 2005; Brimble et al., 2004, Stem Cells 13:585-597). In concordance, chromosome instability and decreased pluripotency of hESCs was reported on cells adapted to grow on TCPS plates and passaged by enzymatic method (Imreh et al., 2006, J. Cell Biochem. 99:508-516).

Pluripotency of hESCs was tested in vitro by embryoid body (EB) formation and identification of genes representative of the three germ line cells: ectoderm (KRT-18), mesoderm (BMP-4) and endoderm (GATA-4) and several other cell-tissue specific genes (FIG. 2B). Occasionally, spontaneous differentiation of hESCs growing on PMEDSAH as well as MATRIGEL was observed at very low rates (<5%). The observed differentiated colonies can be divided into two groups; A) one subpopulation had indistinct borders, with larger cells that migrated away from the colony, and B) another subpopulation of fibroblast-like cells growing between undifferentiated hESC colonies. These fibroblast-like cells were negative for hESC markers. Similar fibroblast-like cells surrounding undifferentiated hESC colonies have been reported previously for feeder-free hESC cultures (Xu et al., 2001, Nat. Biotech. 971-974; Klimanskaya et al., 2005, Lancet 365:1636-1641; Ullmann et al., 2007, Mol. Human. Repro. 13:21-32).

As such, one embodiment the present invention provides synthetic glycoprotein coated substrates, for example PMEDSAH coated substrates, for culturing hESCs wherein the cultured hESCs maintain pluripotency and normal karyotypes. In some embodiments, the PMEDSAH coated surfaces support hESC culture and mechanical propagation for at least 3 passages, at least 5 passages, at least 7 passages, at least 10 passages, at least 15 passages, at least 18 passages over a period of, for example, at least 3 months, at least 5 months, at least 7 months while retaining normal hESC karyotype and pluripotency.

While performing experimentation in development of embodiments of the present invention, phenotypes and genotypes of hESCs cultured on PMEDSAH were basically undistinguishable from those cultured on MATRIGEL. However, interesting differences with respect to the proliferation kinetics were observed between hESCs grown on PMEDSAH and MATRIGEL. For example, while monitored the time between passages (e.g., the time that it takes for a cell population to obtain cell densities sufficient for passaging), colonies grown on PMEDSAH required approximately 17 days to reach their first passage point. Thereafter, passaging points gradually decreased until they reached a plateau of approximately 7 days where it stabilized. In contrast, hESC colonies cultured on MATRIGEL had passaging points after an average of 10 days, and passage points were independent of the passage cycle. A detailed morphological analysis of hESCs cultured on PMEDSAH or MATRIGEL revealed several noteworthy aspects. For example, in contrast to MATRIGEL, where hESCs initially formed small colonies that increased in size and cell number over the next few days (Amit et al., 2003), several embryoid body-like structures and few small colonies were initially observed on the synthetic PMEDSAH hydrogel. Within a few days, growth on PMEDSAH hydrogels demonstrated EB-like structures attached to the hydrogel and hESC proliferation started forming colonies with defined borders and cells with high nucleus to cytoplasm ratio. Additionally, the shape of the initial colonies resembled cell colonies typically encountered for hESCs grown on MEF, and hESCs cultured on the synthetic hydrogel, but not on MATRIGEL, underwent an adaptive growth curve. While all pluripotency markers as well as karyotyping indicates that the undifferentiated cell state of hESCs cultured on PMEDSAH remained unchanged, the gradual decrease of passaging points with increasing passage cycles indicates the ability of hESCs to adapt to this specific synthetic cell matrix.

As described herein, hESCs cultured on PMEDSAH have been propagated for at least eighteen passages during 7 months. All PMEDSAH plates (more than 300 from 20 different batches) successfully support hESC attachment, growth and proliferation, thereby demonstrating that the synthetic substrates as described herein can be synthesized reproducibly with reliability. As well, PMEDSAH-coated plates were stored for several weeks to months and were UV sterilized prior to use, and neither storage nor sterilization negatively affected their ability to support hESC growth and proliferation. In addition, hESCs cultured on PMEDSAH have been cryopreserved using a controlled-rate freezer, thawed, and seeded again effectively on synthetic PMEDSAH matrices.

I. Polymers

As described above, in some embodiments, the present invention provides synthetic polymer substrates for the growth and maintenance of stem cells or embryos. The present invention is not limited to a particular polymer. In certain embodiments, the polymer has a zwitterionic group. In some exemplary embodiments, the zwitterionic group is

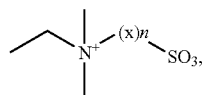

where x is any aliphatic or substituted aliphatic chain, any aryl or substituted aryl chain or hydrogen; and n is an integer of 1 or greater. In some embodiments, the zwitterionic group is MEDSAH. In other embodiments, the zwitterionic group is a zwitterionic group described, for example, in U.S. Pat. No. 6,395,800, herein incorporated by reference.

II. Uses of Synthetic Polymer Substrates

In one embodiment, the present invention provides for synthetic polymer substrates for use in tissue engineering. For example, compositions as described herein find use as a scaffold for growth of cells and tissues for implantation or transplantation into a subject, such as a human. As such, some embodiments of the present invention comprise methods for growing cells and tissues on scaffolds comprising synthetic polymer substrates as defined herein, wherein such scaffolds are used to grow cells in vitro or in vivo. For example, cells and tissues grown on in vitro scaffolds are used to grow cells and tissues for use in, for example research purposes and for implantation or transplantation into subjects as a treatment of a condition or disease. Scaffolds comprising the synthetic polymer matrices as described herein can also be implanted on, or into, a subject thereby aiding in seeding of cells for growth or regeneration of cells and tissues in a particular area or location of a subject to treat a disease or condition.

As such, the present invention provides compositions and methods for defined synthetic substrates for stem cell (e.g., adult or embryonic stem cell) culture, such as PMEDSAH, which represents a system for elimination of xenogeneic components in stem cell derivation and culture. In some embodiments, the present invention provides methods of using the synthetic matrices as described herein to grow and maintain cells (e.g., stem cells such as adult or embryonic stem cells) or embryos useful for fundamental research, cell based therapies, clinical disease applications, therapeutic discoveries, drug screening, toxicology testing, and regenerative medicine. In some embodiments, culture methods utilize fully defined media (e.g., available from Stem Cell Sciences, San Francisco, Calif.), other commercially available media, or other suitable culture media) in combination with the compositions of embodiments of the present invention.

EXPERIMENTAL

The following examples are provided in order to demonstrate and further illustrate certain preferred embodiments and aspects of the present invention and are not to be construed as limiting the scope thereof.

Example 1

Human ESC Culture

Figure 3:
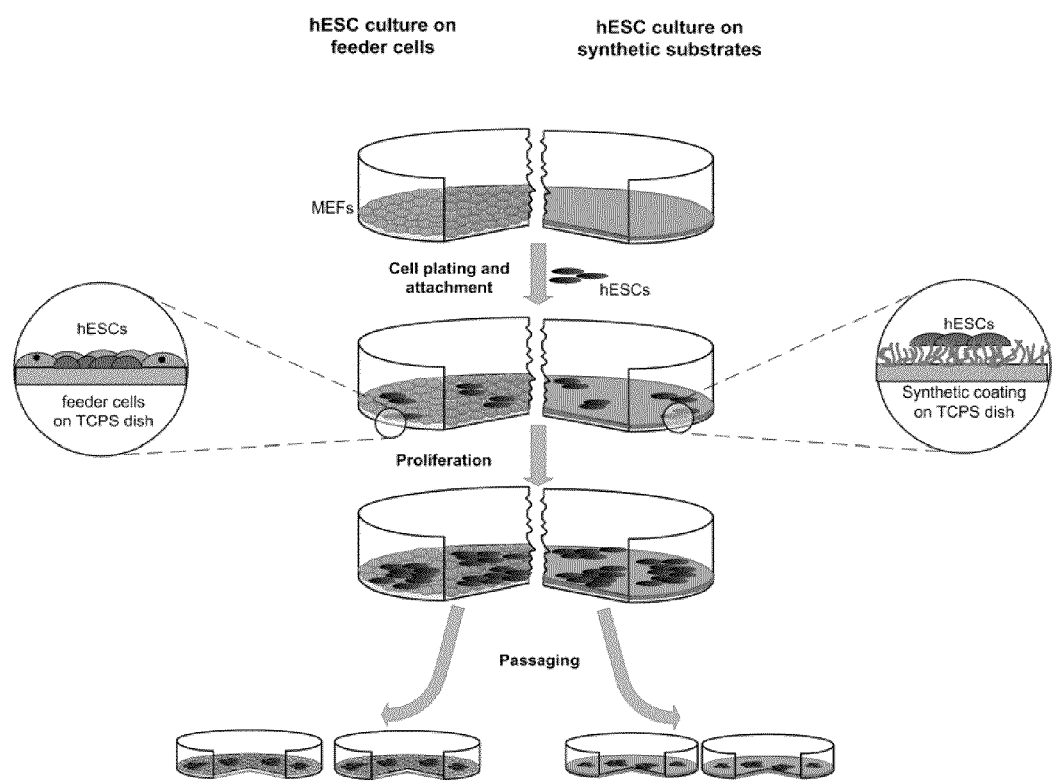
FIG. 3 shows a depiction of the seeding, proliferation and passaging of hESCs cells on MEFs or an exemplary synthetic substrate.

The culture medium for hESCs growing on irradiated mouse embryonic fibroblast (MEF) cells consisted of DMEM/F12 supplemented with 20% knockout serum replacement, 0.1 mM β-mercaptoethanol, 1 mM L-glutamine, 1% nonessential amino acids and 4 ng/ml human recombinant basic fibroblast growth factor. To obtain MEF-conditioned media (MEF-CM), irradiated MEFs ($8 \times 10^6$) were seeded on pre-gelled culture plate dishes. Twenty-four hours after plating, media was replaced for hESC culture media (60 ml), left in contact with MEFs to be conditioned for 24 h, and collected. Mouse embryonic fibroblasts were again fed with hESC culture media daily and used for 4 day CM collection. The CM was frozen at −20° C. until use, and before use it was supplemented with additional 0.1 mM13-mercaptoethanol, 2 mM L-glutamine, and 4 ng/ml bFGF. Passage of undifferentiated colonies was done manually cutting small clumps of cells. Criteria for passage was when greater than 50% of colonies reached a mean diameter of 1 cm or greater and had an architecture of 2-3 cell layers thick (FIG. 3).

Substrates were prepared on tissue culture polystyrene plates (TCPS; 35 mm; Becton Dickinson and Co, Franklin Lakes, N.J.). Bare TCPS and MATRIGEL-coated plates were used as controls. MATRIGEL-coated plates were prepared with MATRIGEL (BD BioSciences, San Jose, Calif.) diluted 1:20 in cold DMEM/F12 at placed at 4° C. overnight, or at room temperature for 2 h. Coating of HEMA, MEDSAH, PEGMA and SMPS onto PTCP was done by activation of the polystyrene surface and initiation of graft-co-polymerization of methacrylate monomers using UV-ozone. Both PLGA and PLA coatings were created by casting polymer films in a Teflon dish and attaching these films to PTCP afterwards.

For MEDSAH, the surface of the substrate was activated using the UV-Ozone generator for 40 min. Graft polymerization onto the polyslyrene surface was carried out at 80° C. with a solution of 0.25M MEDSAH in a 4:1 Mixture of water and ethanol. The polymerization reaction was performed for 2 hours. The substrates were then washed in DI-water at 40-50° C. for 1 hour and dried under nitrogen.

Example 2

Synthetic Substrate Characterization

Coating presences were confirmed using Fourier transformation infrared spectroscopy (FTIR), X-ray photoelectron spectroscopy (XPS), and imaging ellipsometry. Surface morphology of coatings was elucidated using scanning electron microscopy (SEM) and atomic force microscopy (AFM). Synthetic substrates plates were maintained at room temperature in desiccators and were exposed to UV-light for 15 min before using. Prior to cell seeding, all surfaces were washed twice with PBS, MEF-CM was added, and the plates were incubated at 37° C. in 5% $CO_2$ overnight.

Example 3

Immunostaining

Immunostaining on cultured cells was performed to evaluate whether the synthetic substrates could maintain the hESCs in an undifferentiated state. For detecting OCT3/4, SOX-2, SSEA-4, TRA-1-60 and TRA-1-81, cells were fixed with 2% paraformaldehyde at room temperature for 15 min followed by permeabilization with 0.1% Triton X-100 for 10 min. All antibodies were detected with flourescein isothiocyanate (FITC)-labeled secondary antibody except for OCT3/4, which was detected with Texas Red-labeled secondary antibody. Cells were typically evaluation at the $5^{th}$, $10^{th}$ and $15^{th}$ passages. It was determined that the large majority of hESCs remained undifferentiated, with a low incidence (<5%) of spontaneous differentiation observed.

Example 4

In Vitro Evaluation of Pluripotency

Figure 2:
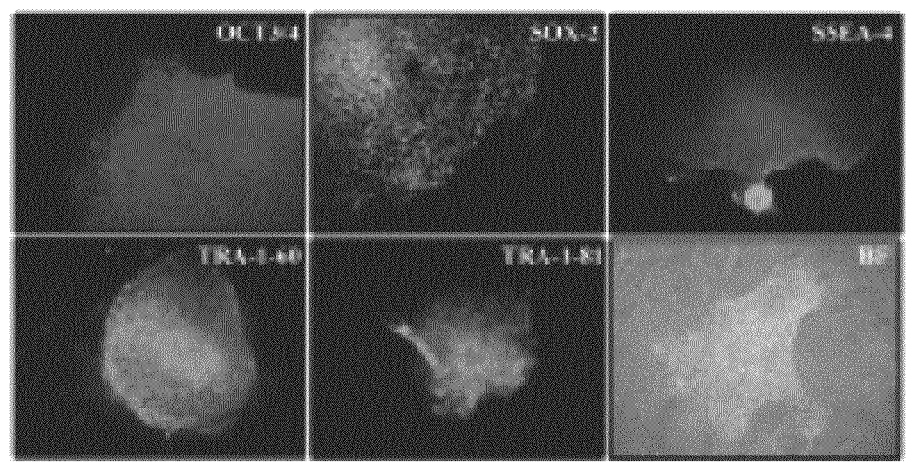
FIG. 2 demonstrates the detection of A) undifferentiated hESC markers as seen in hESCs grown on PMEDSAH coated substrates after multiple passaging. Markers detected include OCT3/4, SOX-2, SSEA-4, TRA-1-60 and TRA-1-81. The sixth frame demonstrates the staining hESC cells for pluripotency and normal colony morphology under phase contrast, and B) RT-PCR expression analysis of pluripotency markers; lane 1-no template control, lane 2-OCT 3/4 and lane 3-SOX-2 from undifferentiated hESC colonies, lane 4-KRT-18 from ectoderm, lane 5-BMP-4 from mesoderm, lane 5-GATA-4 from endoderm found in embryoid bodies, and lane 7-actin control.
Figure 2:
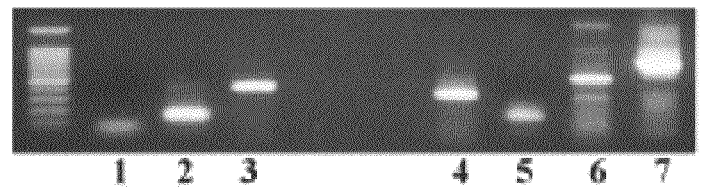

Embryoid bodies derived from clumps were cultured in suspension with culture medium without bFGF for four days and evaluated for pluripotency (FIG. 2, sixth frame).

Example 5

Reverse-transcription PCR Analysis

RT-PCR was performed from total RNA extracted from cells and EBs with TRIzol reagent (Invitrogen) following manufacturers protocol, and SuperScript™ One-Step RT-PCR with Platinum® Taq (Invitrogen) was used for RT-PCR. One microgram of total RNA plus 20 µmol of forward and reverse primers were used in a 50 µl reaction. The cDNA synthesis and pre-denaturation were carried out in one cycle of 48° C. for 45 min, followed by one cycle at 94° C. for 2 min. PCR amplification was performed for 35 cycles at 94° C. for 15 sec, 54° C. for 30 sec, and 72° C. for 1 min. The final extension cycle was 72° C. for 8 min. Ten microliters of each PCR reaction were loaded onto a 1.0% agarose gel and size fractionated. Primers used were; undifferentiation cell markers: OCT 3/4: (f) 5'-ctg cag tgt ggg ttt cgg gca-3' (SEQ ID NO: 1), (r) 5'-ctt gct gca gaa gtg ggt gga gga-3' (SEQ ID NO: 2); and SOX-2: (f) 5'-atg cac cgc tac gac g-3' (SEQ ID NO: 3), (r) 5'-ctt ttg cac ccc tcc cat tt-3' (SEQ ID NO: 4); for endodermal differentiation: GATA4: (f) 5'-ctc ctt cag gca gtg aga gc-3' (SEQ ID NO: 5), (r) 5'-gag atg cag tgt gct cgt gc-3' (SEQ ID NO: 6); for mesodermal differentiation: BMP4: (f) 5'-tga gcc ttt cca gca agt tt-3' (SEQ ID NO: 7), (r) 5'-ctt ccc cgt ctc agg tat ca-3' (SEQ ID NO: 8); for ectodermal differentiation: KRT18: (f) 5'-tct gtg gag aac gac atc ca-3' (SEQ ID NO: 9), (r) 5'-ctg tac gtc tca gct ctg tga-3' (SEQ ID NO: 10); and as a control, β-ACTIN: (f) 5'-atc tgg cac cac acc ttc tac aat gag ctg cg-3' (SEQ ID NO: 11), (r) 5'-cgt cat act cct gct tgc tga tcc aca tct gc-3' (SEQ ID NO: 12).

Example 6

Cytogenetic Analysis

Karyotype of hESCs growing on sulfonated hydrogels at passage 5 and 10 was performed. Chromosome preparation was done using standard protocols and the analysis by GTG banding method. At least 20 cells from each sample were examined by a qualified cytogeneticist.

Example 7

Cryopreservation and Thawing

Cryopreservation by controlled-rate freezing was performed followed a previously established protocol (Ware et al., 2005, Biotechniques 38:879-884), with some modifications. Briefly, clumps were suspended in 250 µl of freezing medium and placed in a 1.2 ml cryovial (Fisher Scientific, Pittsburgh, Pa.). The freezing medium consisted of DMEM (with 4.5 g/L of glucose; Invitrogen), 25% knockout SR (vol/vol), and 10% DMSO (Sigma, St. Louis, Mo.; vol/vol). Cryovials were placed inside a programmable freezing machine (CL-8000, Cryologic, Mulgrave, Victoria, Australia) and lowered from 20° C. to −10° C. at 2° C./min. At −10° C. cryovials were seeded and 5 minutes later the cooling cycle started decreasing 1° C./min to −33° C. Cryovials were then plunged into liquid nitrogen ($LN_2$), held for at least 5 min at −196° C. and maintained in the vapor phase of $LN_2$ ($VLN_2$). Clumps were thawed rapidly by removing the cryovials from $VLN_2$ storage and plunging them directly into 37° C. bath for 1 min. Thawed clumps were washed with culture medium and plated on sulfonated hydrogel plates.

Example 8

Synthetic Polymer Coatings for Long-term Maintenance of Undifferentiated Human Embryonic Stem Cell Growth A. Methods Cell culture. Culture medium for hESCs growing on irradiated MEFs consisted of standard Dulbecco's modified Eagle's medium/F12 (DMEM/F12; GIBCO, Carlsbad, Calif.) supplemented with 20% KnockOut serum replacement (GIBCO), 0.1 mM β-mercaptoethanol, 1 mM L-glutamine, 1% non-essential amino acids and 4 ng/ml human recombinant basic fibroblast growth factor (bFGF) (Xu et al., Nat. Biotechnol. 19:971 [2001]). To obtain MEF-CM, irradiated MEFs ($8\times10^6$ cells) were seeded onto gelatin coated culture dishes in medium composed of high glucose DMEM, 10% fetal bovine serum (FBS), 1% non-essential amino acids, and 200 mM L-glutamine. After 24 h, MEF culture medium was replaced with the hESC culture medium described above (60 ml). This medium was left in contact with MEFs and was collected as MEF-CM after 24 h of conditioning. Media exchange was conducted daily and MEF-CM was collected for 3 days. The MEF-CM was frozen at −20° C. until use, when it was supplemented with 0.1 mM β-mercaptoethanol, 2 mM L-glutamine, and 4 ng/ml bFGF just prior to use (Xu et al., supra). Undifferentiated colonies were mechanically passaged by cutting small clumps of cells when more than 50% of the colonies attained a mean diameter greater than 1 cm and a thickness of 2-3 cell layers.

Cell-culture substrate synthesis. All polymer coatings were prepared on TCPS dishes (35 mm; Becton Dickinson and Co, Franklin Lakes, N.J.). Matrigel-coated and bare TCPS dishes were used as controls. Matrigel (BD BioSciences, San Jose, Calif.) was diluted 1:20 in cold DMEM/F12, applied to the dishes, and coating was allowed to form at 4° C. for overnight or at room temperature for 2 h. Graft-co-polymerization of methacrylate polymers onto TCPS surfaces was carried out using a 0.25 M solution of methacrylate monomers (Sigma-Aldrich, MO) in a 4:1 mixture of water and ethanol (Wu et al., Biomed Microdevices 8:99 [2006]). The TCPS dishes were activated using a UV-ozone generator (Jelight Co. Inc) for 40 min. Surface-activated dishes were immersed into the monomer solution which was heated to 80° C. for 2.5 h. The TCPS dishes were allowed to cool to 50° C. and were rinsed with a warm saline solution (0.9% NaCl, at 50° C.). Polymer coated dishes were left overnight in saline solution at 50° C. The dishes were cleaned by ultra-sonication in DI-water and dried under a stream of nitrogen gas. Both PLA (Sigma-Aldrich, MO) and PLGA (75:25; Sigma-Aldrich, MO) films were cast in a Teflon dish (diameter of 15 cm) by dissolving the polymer (1 g) in chloroform (50 ml) and allowing the solvent to evaporate. The film was carefully peeled off the Teflon dish after 2 days and cut into the requisite size. After extensive washing in DI-water and drying under vacuum, the casted film was attached to the TCPS dish.

Characterization of polymer coatings and preparation for cell culture. Presence of polymer coatings was confirmed using FTIR spectroscopy (Nicolet 6700 spectrometer) in the attenuated total reflectance (ATR) mode with a ZnSe 45° crystal. Elemental analysis was conducted using XPS (Axis Ultra XPS, Kratos Analyticals, UK) equipped with a monochromatized Al Kα X-ray source. The spectra were referenced to an unfunctionalized aliphatic carbon at 285.0 eV. Thickness of the coatings was recorded at a wavelength of 532 nm using $EP^3$—SW imaging ellipsometry (Nanofilm Technology GmbH, Germany). Four-zone nulling was performed at an angle of incidence of 58° and an anisotropic Cauchy parameterization model was used for curve fitting. Surface morphology of coatings was elucidated using SPM. Polymer-coated dishes were stored in desiccators at room temperature. Before cell seeding, dishes were sterilized by exposure to UV-light for 15 min and were washed twice with PBS. Finally dishes were incubated with MEF-CM overnight at 37° C. in a 5% $CO_2$ atmosphere.

Immunostaining. The cells were fixed in 2% paraformaldehyde for 30 min at room temperature and then permeabilized with 0.1% Triton X-100 for 10 min. Primary antibodies were diluted in 1% normal donkey serum and incubated overnight at 4° C. Fluorescein isothiocyanate (FITC)-labeled secondary antibodies were used to detect SOX-2 (Chemicon, Billerica, Mass.), TRA-1-60 (Chemicon), TRA-1-81 (Chemicon) and smooth muscle actin antibodies (DakoCytomation, Denmark). For the detection of OCT3/4 (Santa Cruz Biotechnology Inc., Santa Cruz, Calif.), SSEA-4 (Developmental Studies Hybridoma Bank, Iowa University), β III tubulin (Sigma) and α-fetoprotein (Sigma) antibodies, Texas red-labeled secondary antibodies were used. Samples were imaged using phase-contrast and fluorescent microscopy.

Image analysis. Cell nuclei count was performed with Image J 1.37v on photomicrographs of hESC colonies stained with Hoechst 33258 nuclear staining and either Oct3/4 or Sox-2 antibodies. Then, the percentage of cells positive to either antibody was calculated and compared among colonies culture on PMEDSAH- and Matrigel-coated plates. Unpaired t test was used to calculate the p value.

In vitro evaluation of pluripotency. Pluripotency was evaluated by embryoid body formation at 5, 10, 15 and 20 passages. Embryoid bodies derived from clumps of undifferentiated hESC colonies were cultured in suspension in a medium lacking bFGF to promote differentiation for 10 days. Alternatively, hESCs were allowed to overgrow in differentiation medium for 10 days.

Extraction and purification of total RNA from hESCs and EBs. After manually scrap, cells were pelleted by centrifugation at 800×g in RNase-free, 1.5 ml siliconized microcentrifuge tubes (Ambion, Austin, Tex.). Pellets were disrupted by vigorous pipetting in 800 μl of Trizol Reagent (Invitrogen, Carlsbad, Calif.). This solution was transferred to 2 ml PhaseLoc-Heavy tubes (Eppendorf, Hamburg, Germany), 200 μl of chloroform were added/800 μl of Trizol, and the tubes were centrifuged at maximum speed (13,000×g) in a microcentrifuge. The aqueous phase containing RNA was removed and additionally purified using the RNeasy Mini-Kit (Qiagen, Valencia, Calif.) following the manufacturer's RNA Clean-up protocol with the optional On-column DNase treatment; following the Qiagen protocols. RNA quality was checked using RNA 6000 Nano Assays performed on the Bioanalyzer 2100 Lab-on-a-Chip system (Agilent Technologies, Palo Alto, Calif.).

Reverse-transcription PCR analysis. Total RNA was reverse transcript using SuperScript™ One-Step RT-PCR with Platinum® Taq (Invitrogen) was used. In a single reaction (50 μl), 1 μg of total RNA and 20 pmol of forward (f) and reverse (r) primers were used (Table 4). The cDNA synthesis and pre-denaturation were carried out in the first cycle at 48° C. for 45 min, followed by a second cycle at 94° C. for 2 min. The PCR amplification was performed for 35 cycles at 94° C. for 15 sec, 5° C. for 30 sec, and 72° C. for 1 min. The final extension cycle was operated at 72° C. for 8 min. Finally, 10 μl of PCR reaction products were loaded onto a 1.0% agarose gel and size-fractionated.

Microarray analysis. Total RNA (10 μg) from cells was hybridized to Affymetrix Human Genome U133 Plus 2.0 microarray (Affymetrix; Santa Clara, Calif.) following the manufacturer's instructions. Data analysis was performed using a Robust Multi-array average that converted the plot of perfect match probe into an expression value for each gene (Irizarry et al., Biostatistics 4:249 [2003]). Based on a variance of 0.05, all the probe sets that did not appear to be differentially expressed in any samples were filtered and removed. The fit a linear model were using to increase the power of microarray analysis (Smyth et al., Bioinformatics 21:2067 [2005]).

Microarray validation by real time-PCR analysis. Total RNA was reverse-transcribed using MultiScribe™ Reverse Transcriptase System (Applied Biosystems; Foster city, CA). The ABI 7300 PCR and Detection System (Applied Biosystems) with SYBR® Green PCR Master Mix (Applied Biosystems) was used in real time-PCR. PCR was conducted in triplicate for each sample. Primers were indicated in Table 4. Human Actin was amplified as an internal standard. Reported values were calculated using ΔΔCt method, normalized against endogenous Actin.

Cytogenetic analysis. Karyotype analysis of hESCs was performed at 5, 10, 15 and 20 passages by cytogeneticists at Cell Line Genetics. Chromosomes were prepared using standard protocols and measurement was done using the GTL-banding method on at least 20 cells.

B. Results

Figure 4:
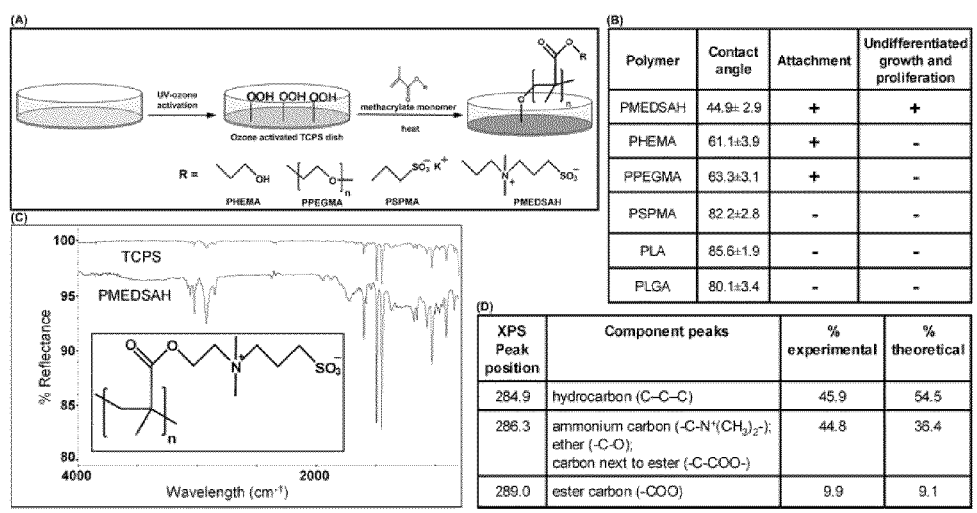
FIG. 4 shows synthesis and characterization of polymer coatings (A) Schematic description of surface-initiated graft-polymerization used to deposit different synthetic polymer coatings onto TCPS dishes. (B) Comparison of the synthetic polymer coatings based on contact angle, attachment of hESCs, and initial undifferentiated growth and proliferation. (C) FT-IR spectrum of PMEDSAH polymer coated and uncoated TCPS surfaces. (D) Characteristic signals from high resolution C1s XPS spectrum of PMEDSAH.

A chemically diverse group of synthetic polymer coatings was selected for cell adhesion studies. To ensure structural consistency between different materials, polymer materials were selected that shared an identical polymer backbone structure, but differed in their side chain chemistries. In addition, the same fabrication method, surface-initiated graft-polymerization, was used to deposit all synthetic polymer coatings onto tissue culture polystyrene (TCPS) dishes (FIG. 4A). As shown in FIG. 4B, differences in side chains result in synthetic polymer coatings with high to moderate hydrophilicity (based on contact angle measurements). Based on side chain chemistries, polymer coatings can be classified as hydrogen-bond acceptors (poly[2-hydroxyethyl methacrylate], PHEMA), hydrogen-bond donors (poly[poly(ethylene glycol) methyl ether methacrylate], PPEGMA), charge-donors (poly[3-sulfopropyl methacrylate], PSPMA), or polyzwitterions (PMEDSAH). This group of polymer coatings was compared to two solvent-cast poly(α-hydroxy esters), PLA and PLGA, as well as Matrigel-coated and unmodified TCPS dishes. Two federal approved hESC lines (H9, NIH code: WA09; WiCell, Madison, Wis.; and BG01, NIH code: BG01; BresaGen, Inc., Athens, Ga.) were used throughout the study. Colonies of hESCs previously cultured on mouse embryonic fibroblasts (MEF) were mechanically harvested and transferred onto polymer-coated cell culture dishes using the approach illustrated in FIG. 3. All cell culture experiments were conducted with MEF-conditioned medium (MEF-CM), which supports hESC growth and proliferation (Xu et al., supra). This approach enables delineation of influences of the matrix versus medium.

During initial cell passages on PLA and PLGA coatings, no hESC attachment was observed. PHEMA, PPEGMA and the negatively-charged PSPMA coatings as well as unmodified TCPS dishes supported initial hESC attachment and proliferation, but the majority of colonies spontaneously differentiated during the first (PPEGMA-coated dishes) or second passage (PHEMA, PSPMA and unmodified TCPS dishes), and propagation of undifferentiated cells was not possible (FIG. 4B). These findings are consistent with a recent study that reported short-term hESC attachment and proliferation on peptide-modified PNIPAAm matrices (Li et al., Journal of Biomedical Materials Research, Part A 79A, 1-5 [2006]). However, a completely different result was observed on PMEDSAH coatings: hESCs not only adhered and proliferated on these surfaces, but also expressed characteristic pluripotent stem cell markers and transcription factors such as OCT3/4, SOX-2, SSEA-4, TRA-1-60 and TRA-1-81, which are associated with the undifferentiated state of hESCs. Based on these short-term adhesion studies, the surfaces were categorized into three groups: (1) Polymer coatings that did not support hESC adhesion (PLA, PLGA, and PSPMA); (2) polymer coatings that supported initial adhesion, but resulted in subsequent differentiation (PEGMA, PHEMA, and TCPS); and (3) polymers that supported adhesion and undifferentiated growth of hESCs (PMEDSAH, Matrigel).

To further characterize the supportive role of PMEDSAH coatings for long-term hESC growth and passaging, a more detailed assessment of the physico-chemical and structural properties of PMEDSAH hydrogel coating was undertaken. One of the most prominent characteristics of PMEDSAH is the presence of zwitterionic sulfobetaine groups. As shown in FIG. 3A, negatively-charged sulfonate and positively-charged quaternary ammonium groups coexist in PMEDSAH in the form of sulfobetaines. This molecular structure results in unusually high localized dipole moments of 23 D23 oriented parallel to the surface while maintaining a net neutral surface. As a result, PMEDSAH can engage in strong inter- and intramolecular dipole interactions, and exist as non-associated as well as fully associated structures (Azzaroni et al., Angewandte Chemie, International Edition 45, 1770-1774 [2006]). Such complex structural behavior is not present in the other synthetic polymer coatings included in this study, but is frequently encountered in naturally-derived materials, such as proteins, which are often considered as prime examples of zwitterionic molecules (Harris et al., Biochemical J. 24:1080 [1930]). Surfaces that present zwitterionic sulfobetaine groups have been used as biomedical coatings or protein-resistant surfaces (Yuan et al., Colloids Surf B Biointerfaces 35, 1-5 [2004]; Jiang et al., Colloids Surf B Biointerfaces 36, 19-26 [2004]; Cho et al., Langmuir 23, 5678-5682 [2007]).

To fabricate synthetic cell culture matrices, PMEDSAH coatings were polymerized on the surfaces of TCPS dishes using a grafting-from approach. Compared to alternate surface modification techniques, such as tethering of polymer chains onto the surface, this approach is known to result in higher surface densities (Zhao et al. Progress in Polymer Sci 25:677 [2000]). After grafting, PMEDSAH coatings were characterized using a combination of surface analytical tools which included X-ray photoelectron microscopy (XPS), Fourier transform infrared spectroscopy (FT-IR), imaging ellipsometry, and scanning probe microscopy (SPM). The polymer coatings had an average thickness of 200 nm, as determined by imaging ellipsometry and an average root mean square (RMS) surface roughness of 0.91 nm, which was determined by SPM. Contact angle measurements revealed an advancing contact angle of 45°, which is in accordance with a self-associated super-coiled regime (Arasawa et al., Reactive and Function Polymers 61: 153 [2004]). On the basis of these data, the resulting polymer coatings are best described as ultra-thin, smooth polymer films consisting of coiled sub-domains chemically tethered to the TCPS surface. Further information regarding the chemical identity of these coatings was revealed by the FT-IR spectrum of the polymer coating (FIG. 4C). Distinct bands were identified at 1724 $cm^{-1}$ and 1196 $cm^{-1}$ indicated the presence of carbonyl groups and sulfonate groups respectively and clearly identified the PMEDSAH polymer coatings. To further confirm initial evidence from FT-IR studies, the elemental composition of PMEDSAH was quantified by means of XPS. Presence of characteristic signals associated with nitrogen were found at 402.0 eV, sulfur at 168.0 eV, and oxygen at 532.0 eV. The relative composition of these elements showed good agreement with the expected chemical composition of PMEDSAH. In addition, the high resolution C1s XPS spectrum of PMEDSAH revealed characteristic signals associated with hydrocarbon (C—H/C) at 285.0 eV, ammonium-bond carbon (—C—N+(CH3)2-) at 286.4 eV, and ester carbon (—COO—) at 288.9 eV (FIG. 4D). Taken together, FT-IR and XPS analyses not only established the chemical composition of PMEDSAH coating, but also provided strong evidence for the presence of zwitterionic groups at the coating surface (Lahann et al., Macromolecules 35:4380 [2002]). Owing to their supportive influence on hESC adhesion and proliferation in short-term experiments together with their unusual chemical properties, PMEDSAH coatings clearly distinguished themselves from other synthetic polymers studied here and elsewhere (Anderson et al., Nature Biotechnology 22:863 [2004]; Ilic, Regenerative Medicine 1:95 [2006]).

Figure 5:
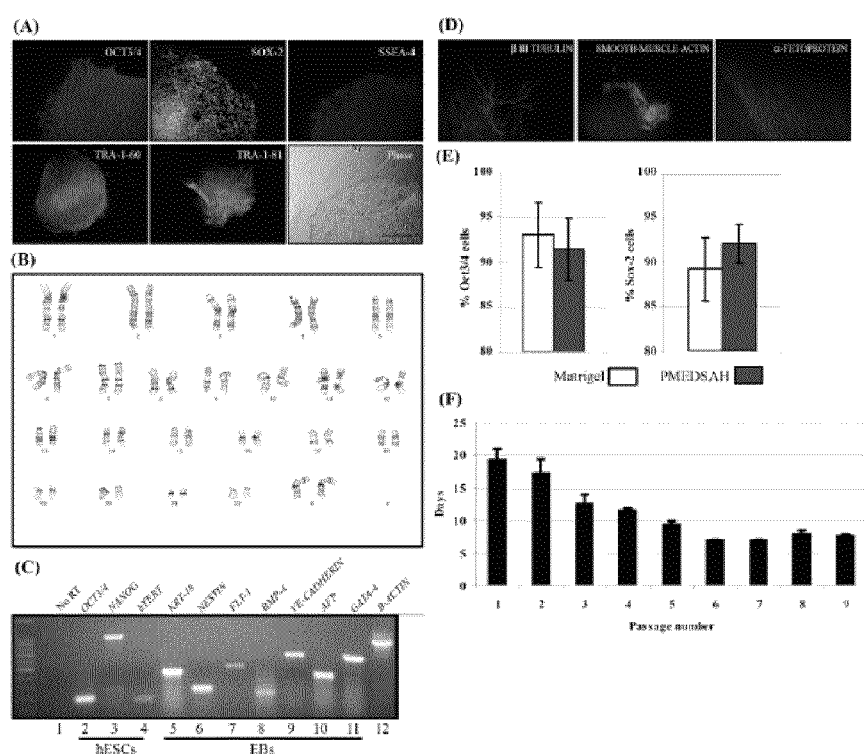
FIG. 5 shows Characterization of hESCs cultured on PMEDSAH. (A) Human ESCs on PMEDSAH expressed ESC markers such as OCT3/4, SOX-2, SSEA-4, TRA-1-60 and TRA-1-81. (B) Standard GTL-banding analysis revealed that hESCs maintained a normal female karyotype throughout the study. (C) RT-PCR analysis of expression of markers of pluripotency (lane 2: OCT3/4; lane 3: NANOG; lane 4: hTERT) from undifferentiated hESC colonies and from ectoderm (lane 5: KRT-18; lane 6: NESTIN), mesoderm (lane 7: FLT-1; lane 8: BMP-4; lane 9: VE-CADHERIN) and endoderm (lane 10: AFP; lane 11: GATA-4) found in EBs. Negative control (Lane 1: no template) and positive control (lane 12: ACTIN). (D) When differentiation was induced in hESCs maintained on PMEDSAH, positive immunoreactivity was identified for β III tubulin, smooth muscle actin and α-fetoprotein, indicating the presence of ectoderm, mesoderm and endoderm respectively. Scale bar is 200 μm. (E) Percentage (average±SEM) of Oct3/4 and Sox-2 positive cells on hESC colonies culture on PMEDSAH- and Matrigel-coated plates at passage 20. (F) Human ESCs growing on PMEDSAH showed an adaptive growth curve and reached a passage-time plateau of 8±1 days (average±SEM).

To evaluate long-term impact of PMEDSAH hydrogel surfaces on stem cell culture, hESCs were mechanically passaged to PMEDSAH- and Matrigel-coated dishes. The cells were monitored at regular intervals using karyotyping, expression of ESC markers and in vitro evaluation of pluripotency. It was found that dishes coated with PMEDSAH supported cell attachment, colony growth, and hESC proliferation for over 8 months. After 5, 10, 15 and 20 passages on PMEDSAH, hESCs were examined by immunostaining, and they expressed pluripotency markers including OCT3/4, SOX-2, SSEA-4, TRA-1-60 and TRA-1-81 (FIG. 5A). Standard GTG-banding analysis, after every fifth passage, revealed that hESCs maintained a normal karyotype (FIG. 5B). Presence of a normal euploid karyotype demonstrates pluripotency. Long-term cultures of mouse31 and human32-35 ESCs have shown to bias for the occurrence of aneuploidy. PMEDSAH coatings have supported hESC culture for 20 passages over a period of 8 months retaining normal karyotype and pluripotency.

The pluripotency of hESCs was further validated in vitro by formation of embryoid bodies and detection of characteristic genes representative of the three embryonic germ layers: ectoderm (KRT-18 and NESTIN), mesoderm (FLT-1, BMP-4 and VE-CADHERIN) and endoderm (AFP and GATA-4) (FIG. 5C). Furthermore, hESCs were allowed to overgrow in a non-supportive medium followed by immunostaining with antibodies specific for β III tubulin (ectoderm), smooth-muscle actin (mesoderm) and α-fetoprotein (endoderm) to identify differentiated cells from the three germ layers (FIG. 5D).

Figure 6:
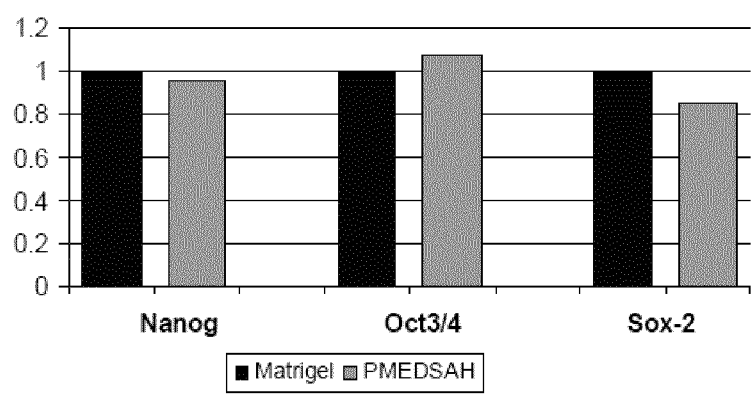
FIG. 6 results from Example 8 showing that genes of pluripotency such as nanog, Oct3/4 and Sox-2 were not significantly different expressed among hESCs cultured on PMEDSAH- and Matrigel-coated dishes.

Throughout this study, phenotypic and genotypic characteristics of hESCs cultured on PMEDSAH coatings were indistinguishable from those on Matrigel-coated dishes. For example, at passage 20 the percentage of cells expressing Oct3/4 and Sox-2 for colonies grown on PMEDSAH-coated dishes was 91.40%±3.43 and 92.06%±2.22 respectively as against 93.00%±3.62 and 89.21%±3.52 for Matrigel-coated dishes (FIG. 5E). Validation by real time PCR analysis verified that genes of pluripotency such as nanog, Oct3/4 and Sox-2 were not significantly different expressed among hESCs cultured on PMEDSAH- and Matrigel-coated dishes (FIG. 6). In addition, microarray analysis was conducted to elucidate mechanistic differences between hESCs grown on PMEDSAH versus Matrigel. Only 23 genes (out of a total of 38,500 genes) were expressed at significantly different (p≤0.05) levels between cells culture on PMEDSAH- and Matrigel-coated dishes. The up and down regulated genes were members of calcium signaling and focal adhesion pathways (Table 2 for genes with identified pathway; Table 3 for complete list of different regulated genes).

While biochemical, histological and genetic analysis showed that hESCs cultured on PMEDSAH and Matrigel are identical, differences with respect to initial proliferation times were observed between hESCs cultured on PMEDSAH and Matrigel coatings. Time between passages, i.e., the time it takes for a cell population to attain cell densities sufficient for passaging, was monitored during long-term cell culture experiments. On Matrigel-coated dishes, hESCs initially formed small colonies that increased in size and cell number over the next few days. Time between passages was 10±2 days, independent of the passage number. On the other hand, hESC colonies cultured on PMEDSAH coatings required culture for 19±3 days prior to the first passage. Thereafter, the time between passages gradually decreased until a plateau of 8±1 days was reached after passage number 7 (FIG. 5E). While the expression of pluripotency markers and the ability to form new colonies indicated that hESCs cultured on PMEDSAH coatings remained undifferentiated, the observed proliferation kinetics show that hESCs cultured on PMEDSAH coatings experienced adaptive growth profiles.

During the course of this study, 300 PMEDSAH hydrogel dishes originating from more than 20 different fabrication batches successfully supported attachment, growth and proliferation of undifferentiated hESCs during 20 continuous passages, an indication that these synthetic substrates can be synthesized in a reproducible and reliable manner. Moreover, long-term storage and UV-sterilization of polymer coated dishes did not affect their ability to support hESC growth and proliferation. In addition, hESCs cultured on PMEDSAH hydrogels were cryopreserved, thawed and successfully re-seeded onto fresh PMEDSAH-coated dishes. Under long-term culture conditions, cells supported by PMEDSAH coatings were phenotypically stable, expressed appropriate pluripotency markers, maintained a normal karyotype, and retained the capacity to differentiate.

Development of PMEDSAH hydrogel coatings as the first fully-defined synthetic substrate for long-term hESC culture represents important progress toward the elimination of xenogenic, undefined, and labile components from the insoluble microenvironment used for hESC derivation and culture. This rationally designed culture matrix establishes a radical, rather than incremental diversion from previously exploited hESC support matrices and provides one of the missing links in future development of fully defined hESC microenvironments. A major advantage of fully synthetic matrices over naturally derived substrates is that there physico-chemical makeup can be altered in highly controlled ways opening the possibilities for more detailed mechanistic studies that not only aim at understanding the mechanisms behind the novel capabilities of PMEDSAH, but ultimately lead to entirely defined microenvironments consisting of synthetic matrices and synthetic media.

TABLE 2

| Pathway | Description | GenBank | Fold change |
| --- | --- | --- | --- |
| Jak-STAT signaling pathway | Suppressor of cytokine signaling 3 | AI244908 | −1.88 |
| Neuroactive ligand-receptor interaction | Neuropeptide FF receptor 2 | AF257210 | −1.75 |
| Calcium signaling pathway | Guanine nucleotide binding protein (G protein), alpha 14 | NM_004297 | −1.55 |
| Biosynthesis of steroids and terpenoid | Farnesyl-diphosphate farnesyltranferase 1 | BF438300 | −1.52 |
| Focal adhesion | Caveolin 1, caveolae protein, 22 kDa | NM_001753 | −1.48 |
| Purine, pyrimidine, nicotinate and nicotinamide metabolism | 5'-nucleotidase cytosolic II | AV700081 | −1.43 |
| Jak-STAT signaling pathway, cytokine-cytokine receptor interaction | Interleukin 13 receptor, alpha 1 | U81380 | −1.42 |

TABLE 2-continued

| Pathway | Description | GenBank | Fold change |
|---|---|---|---|
| Notch signaling pathway | Mastermind-like 2 (*Drosophila*) | BF358386 | −1.31 |
| Calcium signaling pathway, gap junction | GNAS complex locus | AF107846 | 1.52 |

TABLE 3

| Pathway | Description | GenBank | Fold change |
|---|---|---|---|
| | Annexin A3 | M63310 | −2.01 |
| Jak-STAT signaling pathway | Suppresor of cytokine signaling 3 | AI244908 | −1.88 |
| Neuroactive ligand-receptor interaction | Neuropeptide FF receptor 2 | AF257210 | −1.75 |
| | Glycoprotein M6A | D49958 | −1.66 |
| | | BC039495 | −1.62 |
| Calcium signaling pathway | Guanine nucleotide binding protein (G protein), alpha 14 | NM_004297 | −1.55 |
| Biosynthesis of steroids and terpenoid | Farnesyl-diphosphate farnesyltransferase 1 | BF438300 | −1.52 |
| Focal adhesion | Caveolin 1, caveolae protein, 22 kDa | NM_001753 | −1.48 |
| | Caldesmon 1 | NM_018495 | −1.47 |
| Purine, pyrimidine, nicotinate and nicotinamide metabolism | 5′-nucleotidase cytosolic II | AV700081 | −1.43 |
| | | AL157496 | −1.43 |
| | Glypican 6 | AK021505 | −1.42 |
| | Nuclear factor I/B | AI186739 | −1.42 |
| Jak-STAT signaling pathway, cytokine-cytokine receptor interaction | Interleukin 13 receptor, alpha 1 | U81380 | −1.42 |
| | Supervillin | NM_003174 | −1.40 |
| | Chromosome 6 open reading frame 155 | BF500942 | −1.39 |
| | | AF194537 | −1.36 |
| Notch signaling pathway | Mastermind-like 2 (*Drosophila*) | BF358386 | −1.31 |
| | Zinc finger protein 342 | AA761573 | 1.30 |
| | Transcription elongation factor A (S-II)-like 2 | AF063606 | 1.36 |
| | Cripto, PRL-1, cryptic family 1 | AF312769 | 1.40 |
| Calcium signaling pathway, gap junction | GNAS complex locus | AF107846 | 1.52 |
| | Zinc finger and BTB domain containing 24 | BC036731 | 1.55 |

TABLE 4

| Gene | Forward primer | Seq. ID | Reverse primer | Seq. ID | Product (bp) |
|---|---|---|---|---|---|
| Reverse Transcriptase | | | | | |
| OCT3/4 | ctgcagtgtgggtttcgggca | 1 | cttgctgcagaagtgggtggagga | 2 | 168 |
| NANOG | cggcttcctcctcttcctctatac | 13 | atcgatttcactcatcttcacacgtc | 14 | 953 |
| hTERT | cggaagagtgtctggagcaa | 15 | ggatgaagcggagtctgga | 16 | 144 |
| KRT18 | tctgtggagaacgacatcca | 9 | ctgtacgtctcagctctgtga | 10 | 378 |
| NESTIN | cagctggcgcacctcaagatg | 17 | agggaagttgggctcaggactgg | 18 | 209 |
| BMP4 | tgagcctttccagcaagttt | 7 | cttccccgtctcaggatatca | 8 | 182 |
| VE-CADHERIN | acgggatgaccaagtacagc | 19 | acacactttgggctggtagg | 20 | 593 |
| FLT-1 | atcagagatcaggaagcacc | 21 | ggaacttcatctgggtccat | 22 | 451 |
| AFP | ccatgtacatgagcactgttg | 23 | ctccaataactcctggtatcc | 24 | 357 |
| GATA-4 | ctccttcaggcagtgagagc | 5 | gagatgcagtgtgctcgtgc | 6 | 574 |
| ACTIN | atctggcaccacaccttctacaatgagctgcg | 11 | cgtcatactcctgcttgctgatccacatctgc | 12 | 835 |

TABLE 4-continued

| Gene | Forward primer | Seq. ID | Reverse primer | Seq. ID | Product (bp) |
|---|---|---|---|---|---|
| Real-time PCR | | | | | |
| SOX2 | gagagaaagaaagggagagaag | 25 | gagagaggcaaactggaatc | 26 | 140 |
| NANOG | tcctcctcttcctctatactaac | 27 | cccacaaatcaggcatag | 28 | 112 |
| OCT3/4 | agtcagtgaacagggaatgg | 29 | tcgggattcaagaacctcg | 30 | 131 |
| Actin | gccgaggactttgattgc | 31 | gtgtggacttgggagagg | 32 | 143 |

TABLE 5

| Substrate | Contact angle (in dry state) | Percentage (±SEM) of attachment and colony formation | Percentage (±SEM) of cells positive to Oct3/4 | Sox-2 | Number of passages |
|---|---|---|---|---|---|
| Matrigel | Nm | 98 ± 2 | 93 ± 3.6 | 89.2 ± 3.5 | 20 |
| PMEDSAH | 17.1 ± 1.2 | 15 ± 1 | 91.4 ± 3.4 | 92.06 ± 2.2 | 20-still in progress |
| PHEMA | 56.0 ± 1.4 | 12 ± 1 | 0 | 0 | 2 |
| PPEGMA | 63.3 ± 3.1 | 5 ± 1 | 0 | 0 | 1 |
| PSPMA | 50.2 ± 4.1 | 14 ± 2 | — | 91 ± 5 | 2-still in progress |
| PLA | 85.6 ± 1.9 | 0 | — | — | 0 |
| PLGA | 80.1 ± 3.4 | 0 | — | — | 0 |
| PMAPDSAH | 69.2 ± 4.7 | 7 ± 2 | — | — | Still in progress |
| PCBMA | 71.6 ± 4.9 | 0 | | | |
| PMETAC | 40.5 ± 5.8 | 8 ± 1 | 90 ± 2.3 | 90 ± 5.2 | 2-still in progress |
| TCPS | Nm | 8 ± 2 | 0 | 0 | 0 |

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for culturing human pluripotent stem cells comprising:
   a) applying human pluripotent stem cells to a substrate, wherein said substrate comprises poly[2-(methacryloyloxy)ethyl dimethyl(3-sulfopropyl)ammonium] (PMEDSAH); and
   b) growing said human stem cells on said substrate in the presence of culture media capable of maintaining said cells.

2. The method of claim 1, wherein said human pluripotent stem cells are embryonic stem cells.

3. The method of claim 1, wherein said human pluripotent stem cells maintain pluripotency after at least 5 passages.

* * * * *

SEQUENCE LISTING

<160> NUMBER OF SEQ ID NOS: 32

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
ctgcagtgtg ggtttcgggc a           21

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
cttgctgcag aagtgggtgg agga         24

<210> SEQ ID NO 3
<211> LENGTH: 16

```
<212> TYPE: DNA
<213> ORGANISM: Artificial Sequence
<220> FEATURE:
<223> OTHER INFORMATION: Synthetic

<400> SEQUENCE: 3
atgcaccgct acgacg                                                   16

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
cttttgcacc cctcccattt                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ctccttcagg cagtgagagc                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
gagatgcagt gtgctcgtgc                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
tgagcctttc cagcaagttt                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
cttccccgtc tcaggtatca                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
```
tctgtggaga acgacatcca                                              20

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
ctgtacgtct cagctctgtg a                                            21

<210> SEQ ID NO 11
<211> LENGTH: 32
<212> TYPE: DNA
<213> ORGANISM: Artificial Sequence
<220> FEATURE:
<223> OTHER INFORMATION: Synthetic

<400> SEQUENCE: 11
atctggcacc acaccttcta caatgagctg cg                                32

<210> SEQ ID NO 12
<211> LENGTH: 32
<212> TYPE: DNA
<213> ORGANISM: Artificial Sequence
<220> FEATURE:
<223> OTHER INFORMATION: Synthetic

<400> SEQUENCE: 12
cgtcatactc ctgcttgctg atccacatct gc                                32

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13
cggcttcctc ctcttcctct atac                                         24

<210> SEQ ID NO 14
<211> LENGTH: 26
<212> TYPE: DNA
<213> ORGANISM: Artificial Sequence
<220> FEATURE:
<223> OTHER INFORMATION: Synthetic

<400> SEQUENCE: 14
atcgatttca ctcatcttca cacgtc                                       26

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
cggaagagtg tctggagcaa                                              20

<210> SEQ ID NO 16
<211> LENGTH: 19
<212> TYPE: DNA
<213> ORGANISM: Artificial Sequence
<220> FEATURE:
<223> OTHER INFORMATION: Synthetic

<400> SEQUENCE: 16
ggatgaagcg gagtctgga                                             19

<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
cagctggcgc acctcaagat g                                          21

<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18
agggaagttg ggctcaggac tgg                                        23

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
acgggatgac caagtacagc                                            20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
acacactttg ggctggtagg                                            20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
atcagagatc aggaagcacc                                            20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
ggaacttcat ctgggtccat                                            20

```
<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23
ccatgtacat gagcactgtt g                                      21

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
ctccaataac tcctggtatc c                                      21

<210> SEQ ID NO 25
<211> LENGTH: 22
<212> TYPE: DNA
<213> ORGANISM: Artificial Sequence
<220> FEATURE:
<223> OTHER INFORMATION: Synthetic

<400> SEQUENCE: 25
gagagaaaga aagggagaga ag                                     22

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
gagagaggca aactggaatc                                        20

<210> SEQ ID NO 27
<211> LENGTH: 23
<212> TYPE: DNA
<213> ORGANISM: Artificial Sequence
<220> FEATURE:
<223> OTHER INFORMATION: Synthetic

<400> SEQUENCE: 27
tcctcctctt cctctatact aac                                    23

<210> SEQ ID NO 28
<211> LENGTH: 18
<212> TYPE: DNA
<213> ORGANISM: Artificial Sequence
<220> FEATURE:
<223> OTHER INFORMATION: Synthetic

<400> SEQUENCE: 28
cccacaaatc aggcatag                                          18

<210> SEQ ID NO 29
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 29
agtcagtgaa cagggaatgg                                              20

<210> SEQ ID NO 30
<211> LENGTH: 19
<212> TYPE: DNA
<213> ORGANISM: Artificial Sequence
<220> FEATURE:
<223> OTHER INFORMATION: Synthetic

<400> SEQUENCE: 30
tcgggattca agaacctcg                                               19

<210> SEQ ID NO 31
<211> LENGTH: 18
<212> TYPE: DNA
<213> ORGANISM: Artificial Sequence
<220> FEATURE:
<223> OTHER INFORMATION: Synthetic

<400> SEQUENCE: 31
gccgaggact ttgattgc                                                18

<210> SEQ ID NO 32
<211> LENGTH: 18
<212> TYPE: DNA
<213> ORGANISM: Artificial Sequence
<220> FEATURE:
<223> OTHER INFORMATION: Synthetic

<400> SEQUENCE: 32
gtgtggactt gggagagg                                                18
```